(12) United States Patent
Kuznetsov et al.

(10) Patent No.: US 9,291,554 B2
(45) Date of Patent: Mar. 22, 2016

(54) METHOD OF ELECTROMAGNETIC MODELING OF FINITE STRUCTURES AND FINITE ILLUMINATION FOR METROLOGY AND INSPECTION

(71) Applicants: Alexander Kuznetsov, Mountain View, CA (US); Kevin Peterlinz, Fremont, CA (US); Andrei Shchegrov, Campbell, CA (US); Leonid Poslavsky, Belmont, CA (US); Xuefeng Liu, San Jose, CA (US)

(72) Inventors: Alexander Kuznetsov, Mountain View, CA (US); Kevin Peterlinz, Fremont, CA (US); Andrei Shchegrov, Campbell, CA (US); Leonid Poslavsky, Belmont, CA (US); Xuefeng Liu, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/170,150

(22) Filed: Jan. 31, 2014

(65) Prior Publication Data
US 2014/0222380 A1 Aug. 7, 2014

Related U.S. Application Data

(60) Provisional application No. 61/761,146, filed on Feb. 5, 2013.

(51) Int. Cl.
*G01N 21/84* (2006.01)
*G01B 21/30* (2006.01)
(Continued)

(52) U.S. Cl.
CPC ............ *G01N 21/4788* (2013.01); *G01B 21/30* (2013.01); *G01N 21/84* (2013.01);
(Continued)

(58) Field of Classification Search
CPC ........ G01B 11/00; G01B 11/30; G01B 15/00; G01B 15/08; G01B 21/00; G01B 21/30; G01B 21/84; G01B 21/8411; G01B 21/8416; G01D 7/00; G01D 9/00; G01D 21/00; G01N 21/00; G01N 21/17; G01N 21/27; G01N 21/47; G01N 23/00; G01N 23/22; G06F 11/30; G06F 11/32; G06F 11/34; G06F 15/00; G06F 15/16; G06F 17/00; G06F 17/10; G06F 17/40; G06F 17/50; G06F 19/00
USPC ........ 73/432.1, 865.8, 865.9, 866.3; 250/306, 250/307; 356/237.1, 237.2, 237.3, 237.4, 356/237.5, 337; 378/1, 70, 71, 82, 86, 162; 382/100, 141, 145, 152; 702/1, 81, 82, 702/83, 84, 127, 182, 187, 189; 708/100, 708/105, 200
See application file for complete search history.

(56) References Cited

U.S. PATENT DOCUMENTS 2,767,914 A * 10/1956 Merrill et al. ................... 702/82
2,798,966 A * 7/1957 Summerhayes, Jr .... 250/559.08
(Continued)

FOREIGN PATENT DOCUMENTS

| RU | 2223462 | 10/2004 |
|---|---|---|
| RU | 2373494 | 11/2009 |
| WO | WO-2012095808 | 7/2012 |

OTHER PUBLICATIONS

International Search Report and Written Opinion from PCT/US2014/014680 mailed May 30, 2014, 9 pages.
(Continued)

*Primary Examiner* — Edward Cosimano
(74) *Attorney, Agent, or Firm* — Blakely Sokoloff Taylor Zafman LLP

(57) ABSTRACT

Electromagnetic modeling of finite structures and finite illumination for metrology and inspection are described herein. In one embodiment, a method for evaluating a diffracting structure involves providing a model of the diffracting structure. The method involves computing background electric or magnetic fields of an environment of the diffracting structure. The method involves computing scattered electric or magnetic fields from the diffracting structure using a scattered field formulation based on the computed background fields. The method further involves computing spectral information for the model of the diffracting structure based on the computed scattered fields, and comparing the computed spectral information for the model with measured spectral information for the diffracting structure. In response to a good model fit, the method involves determining a physical characteristic of the diffracting structure based on the model of the diffracting structure.

23 Claims, 12 Drawing Sheets

(51) Int. Cl.
*G06F 17/40* (2006.01)
*G06F 19/00* (2011.01)
*G01N 21/47* (2006.01)
*G01N 21/956* (2006.01)
*G03F 7/20* (2006.01)

(52) U.S. Cl.
CPC ...... *G01N21/95607* (2013.01); *G03F 7/70625* (2013.01); *G01N 2021/95615* (2013.01); *G06F 17/40* (2013.01); *G06F 19/00* (2013.01)

(56) References Cited

U.S. PATENT DOCUMENTS

| | | | | |
|---|---|---|---|---|
| 3,176,306 | A * | 3/1965 | Burns | 346/33 F |
| 3,526,836 | A * | 9/1970 | Erturk et al. | 324/73.1 |
| 6,297,880 | B1 | 10/2001 | Rosencwaig et al. | |
| 6,429,943 | B1 | 8/2002 | Opsal et al. | |
| 6,654,131 | B2 | 11/2003 | Psal et al. | |
| 6,819,426 | B2 * | 11/2004 | Sezginer et al. | 356/401 |
| 6,829,057 | B2 | 12/2004 | Opsal et al. | |
| 6,972,852 | B2 | 12/2005 | Opsal et al. | |
| 7,042,569 | B2 * | 5/2006 | Sezginer et al. | 356/401 |
| 7,171,284 | B2 | 1/2007 | Vuong et al. | |
| 7,202,958 | B1 | 4/2007 | McGahan | |
| 7,248,375 | B2 | 7/2007 | Opsal et al. | |
| 7,289,213 | B2 | 10/2007 | Mieher et al. | |
| 7,372,565 | B1 | 5/2008 | Holden et al. | |
| 7,388,677 | B2 | 6/2008 | Vuong et al. | |
| 7,454,103 | B2 | 11/2008 | Parriaux | |
| 7,502,101 | B2 | 3/2009 | Raymond et al. | |
| 7,528,941 | B2 | 5/2009 | Kandel et al. | |
| 7,528,953 | B2 | 5/2009 | Frommer et al. | |
| 7,567,351 | B2 | 7/2009 | Opsal et al. | |
| 7,602,509 | B1 | 10/2009 | Hench | |
| 7,615,752 | B2 | 11/2009 | Raymond et al. | |
| 7,751,046 | B2 | 7/2010 | Levy et al. | |
| 8,675,188 | B2 * | 3/2014 | Liu et al. | 356/237.4 |
| 8,982,358 | B2 | 3/2015 | Shchegrov et al. | |
| 2002/0158193 | A1 * | 10/2002 | Sezginer et al. | 250/237 G |
| 2003/0197872 | A1 * | 10/2003 | Littau et al. | 356/625 |
| 2005/0018190 | A1 * | 1/2005 | Sezginer et al. | 356/401 |
| 2008/0249754 | A1 | 10/2008 | Niu et al. | |
| 2009/0083013 | A1 | 3/2009 | Li et al. | |
| 2009/0198635 | A1 | 8/2009 | Doddi et al. | |
| 2011/0137625 | A1 | 6/2011 | Dirks et al. | |
| 2013/0182263 | A1 | 7/2013 | Shchegrov et al. | |
| 2013/0215420 | A1 * | 8/2013 | Liu et al. | 356/237.5 |

OTHER PUBLICATIONS

D. G. Flagello, et al., "Theory of high-NA imaging in homogeneous thin films," J. Opt. Soc. Am. A 13, 53-64, Jan. 1996.

N. Kumar, at al., "Coherent Fourier Scatterometry (Tool for Improved Sensitivity in Semiconductor Metrology)" Proceedinas of SPIE, vol. 8324 83240Q-1 http://spiedigitallibrary.org/, Accessed on Jun. 10, 2013, 2012 8 pages.

"Computational Exectrodynamics: The Finite-Difference Time-Domain Method", Taflove, A. and Hagness, S. C., 3rd ed., Artech House, Boston, MA, 2005, pp. 107-144 and 227-280.

"Domain Decomposition Methods—Algorithms and Theory", Adrea Toselli and Olof Widlund, Springer Series in Computational Mathematics, vol. 34, 2004, pp. 311-335.

"Principles of Optics: Electromagnetic Theory of Propagation, Interference and Diffraction of Light", Born, Max and Wolf, Emil (1999), 7th Ed., Cambridge: Cambridge University Press, pp. 695-734.

U.S. Appl. No. 13/924,204, Optical metrology of periodic targets in presence of multiple diffraction orders, filed Jun. 21, 2013.

* cited by examiner

METHOD OF ELECTROMAGNETIC MODELING OF FINITE STRUCTURES AND FINITE ILLUMINATION FOR METROLOGY AND INSPECTION

PRIORITY

This application is a Non-Provisional of, claims priority to, and incorporates by reference in its entirety for all purposes, U.S. Provisional Patent Application No. 61/761,146 filed Feb. 5, 2013.

TECHNICAL FIELD

Embodiments of the invention pertain to methods of electromagnetic modeling, and in particular to electromagnetic modeling of finite structures and finite illumination for metrology and inspection.

BACKGROUND

Optical metrology techniques offer the potential to characterize parameters of a workpiece (i.e., a sample) during a manufacturing process. For example, in scatterometry, light is directed onto a periodic grating formed in a workpiece and spectra of reflected light are measured and analyzed to characterize the grating. Characterization parameters may include critical dimensions (CDs), sidewall angles (SWAs) and heights (HTs) of gratings, material dispersion parameters, and other parameters that affect the polarization and intensity of the light reflected from or transmitted through a material. Characterization of the grating may thereby characterize the workpiece as well as the manufacturing process employed in the formation of the grating and the workpiece.

For example, the optical metrology system 100 depicted in FIG. 1A can be used to determine the profile of a grating 102 formed on a semiconductor wafer 104. The grating 102 can be formed in test areas on the wafer 104, such as adjacent to a device formed on the wafer 104. The optical metrology system 100 can include a photometric device with a source 106 and a detector 112. The optical metrology system 100 illuminates the grating 102 with an incident beam 108 from a source 106. In the illustrated embodiment, the optical metrology system 100 directs the incident beam 108 onto the grating 102 at an angle of incidence O with respect to a normal of the grating 102 and an azimuth angle $\phi$ (e.g., the angle between the plane of incidence beam 108 and the direction of the periodicity of the grating 102). A diffracted beam 110 leaves at an angle $\theta_d$ with respect to the normal and is received by the detector 112. The detector 112 converts the diffracted beam 110 into a measured metrology signal including spectral information. To determine the profile of the grating 102, the optical metrology system 100 includes a processing module 114 configured to receive the measured metrology signal and analyze the measured metrology signal.

Analysis of the measured metrology signal generally involves comparing the measured sample spectral information to simulated spectral information to deduce a scatterometry model's parameter values that best describe the measured sample. Typically, rigorous coupled-wave analysis (RCWA) is used for solving light scattering problems in such metrology applications. RCWA is a Fourier-space method that relies on representing the fields as a sum of spatial harmonics. One limitation of RCWA is the assumption of infinite, periodic target structures and infinite illuminating beams. Another disadvantage of existing methods using RCWA is that one simulation is generally required for each angle of incidence (AOI). Therefore, evaluation of a diffracting structure may require a large number of simulations, which may make existing methods impractical for applications requiring fast inspection such as high-volume semiconductor manufacturing.

BRIEF DESCRIPTION OF THE DRAWINGS

Embodiments of the present invention are illustrated by way of example, and not by way of limitation, in the figures of the accompanying drawings, in which.

DETAILED DESCRIPTION

Figure 1A:
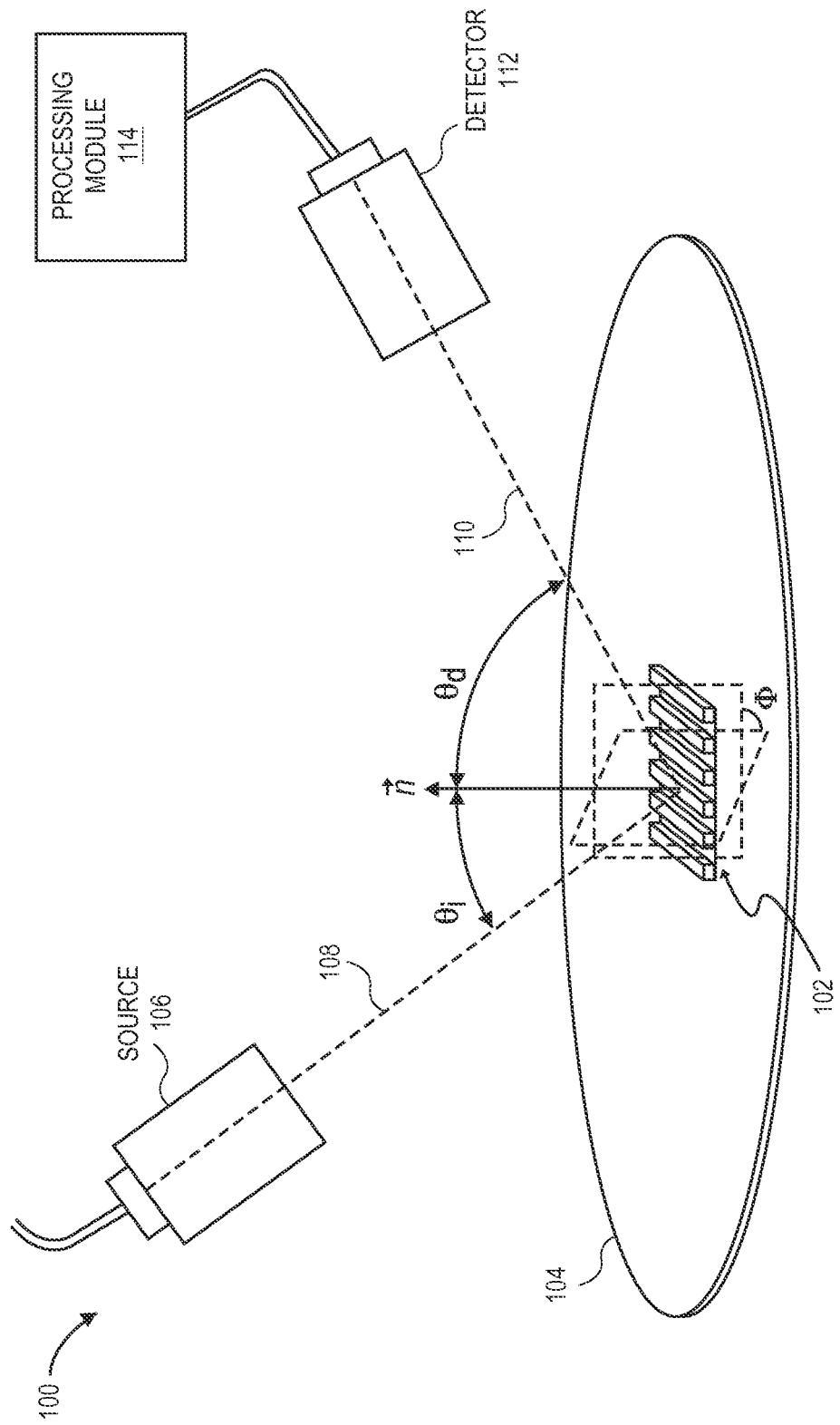
FIG. 1A depicts an optical metrology system for scatterometry.

Embodiments of the invention include methods, apparatuses, and systems for electromagnetic modeling of finite structures and finite illumination for metrology and inspection. In one embodiment, a method of evaluating a diffracting structure involves providing a model of the diffracting structure and computing background electric or magnetic fields of an environment of the diffracting structure. The method involves computing scattered electric or magnetic fields from the diffracting structure using a scattered field formulation based on the computed background fields. The method involves computing spectral information for the model of the diffracting structure based on the computed scattered fields, and comparing the computed spectral information for the model with measured spectral information for the diffracting structure. In response to a good model fit, the method further involves determining a physical characteristic of the diffracting structure based on the model of the diffracting structure.

Embodiments enable modeling of non-periodic structures and realistic (e.g., non-plane wave) illumination beams. Embodiments may therefore provide for the capability of modeling electromagnetic wave's scattering from isolated structures and individual defects, as well as simulation of roughness effects (e.g., line edge roughness). Additionally, embodiments enable modeling multiple angles of incidence in one simulation, which can provide significant increases in computational speed. In comparison to conventional approaches involving a simulation for each angle of incidence, assuming N pupil samples per wavelength, embodiments may result in a speed up of at least N times, while also achieving higher precision than conventional approaches.

Furthermore, embodiments involving spatial domain methods may enable improved computational speed when, for example, the target contains metals or high-K materials. In contrast to existing RCWA methods, which generally require high truncation orders for accurate modeling of such targets and exhibit poor convergence, embodiments involving spatial domain methods are unaffected by the high absorption of such targets.

In the following description, numerous details are set forth. It will be apparent, however, to one skilled in the art, that the present invention may be practiced without these specific details. For example, while some embodiments are described in the context of scatterometry for diffraction grating parameter measurements, it should be appreciated that the methods may be readily adaptable to other contexts and applications by one of ordinary skill in the art. For example, embodiments described herein may be used in metrology systems using spectroscopic ellipsometry, spectroscopic reflectometry, spectroscopic scatterometry, scatterometry overlay, beam profile reflectometry, beam profile ellipsometry, and single- or multiple-discrete wavelength ellipsometry.

In some instances, well-known methods and devices are shown in block diagram form, rather than in detail, to avoid obscuring the present invention. Reference throughout this specification to "an embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not mutually exclusive.

Some portions of the detailed descriptions provide herein are presented in terms of algorithms and symbolic representations of operations on data bits within a computer memory. Unless specifically stated otherwise, as apparent from the following discussion, it is appreciated that throughout the description, discussions utilizing terms such as "calculating," "computing," "determining" "estimating" "storing" "collecting" "displaying," "receiving," "consolidating," "generating," "updating," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices. As used herein, "model" refers to a scatterometry model or other optical model and "parameter" refers to a model parameter unless otherwise specified. Although some of the following examples are described in terms of a Cartesian coordinate system, other coordinate systems may be used.

Figure 1B:
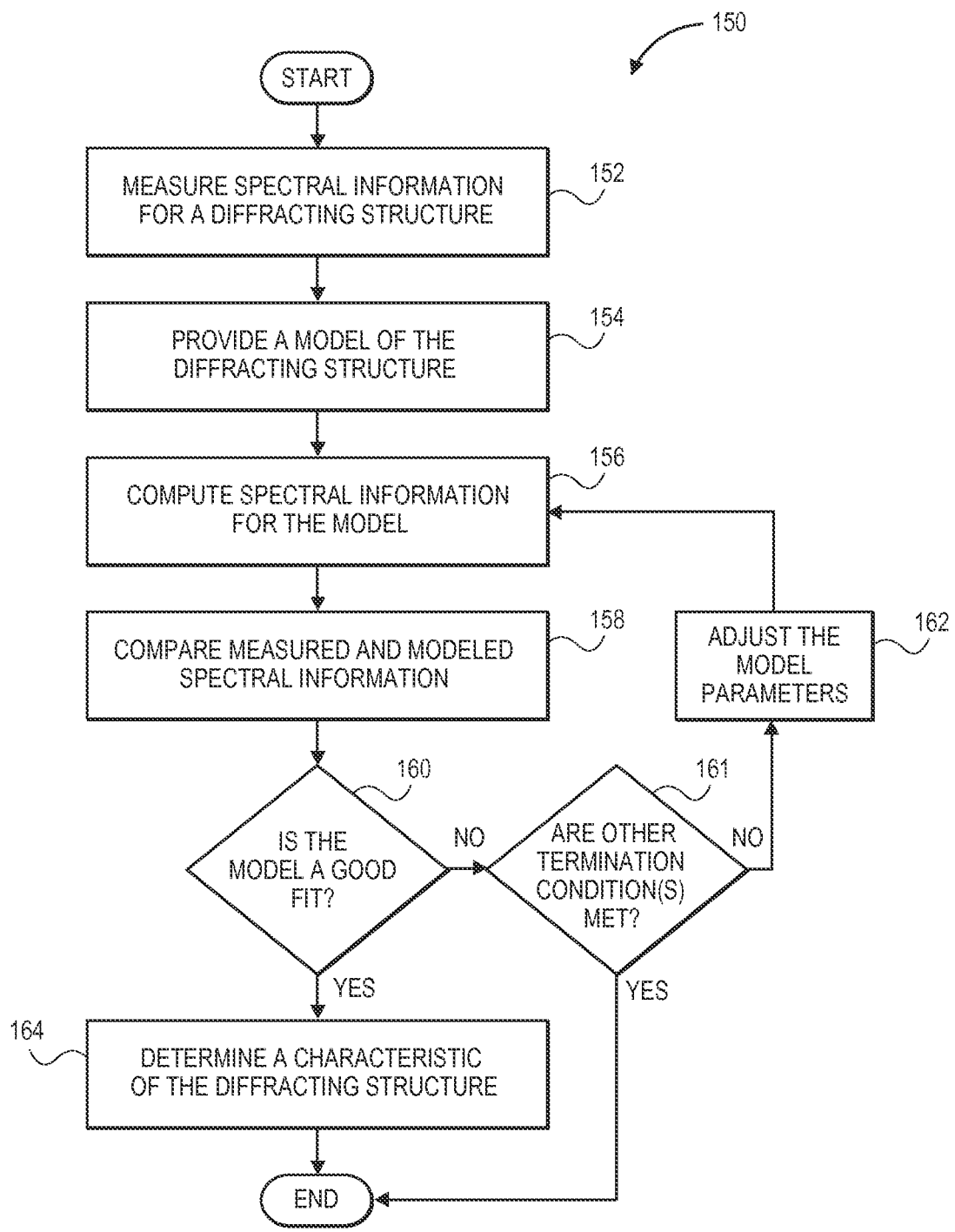
FIG. 1B is a flow diagram illustrating a general method for evaluating a diffracting structure, in accordance with an embodiment of the invention.

FIG. 1B is a flow diagram illustrating a general method for evaluating a diffracting structure, in accordance with an embodiment of the invention. The method 150 of FIG. 1B may be performed by an optical metrology system. An optical metrology system may include a processing module, a light source for illuminating a sample, and a detector for measuring reflected light, such as the system 100 of FIG. 1A. Additionally or alternatively, an optical metrology system may include components such as in the optical metrology system 1100 of FIG. 11.

Figure 3A:
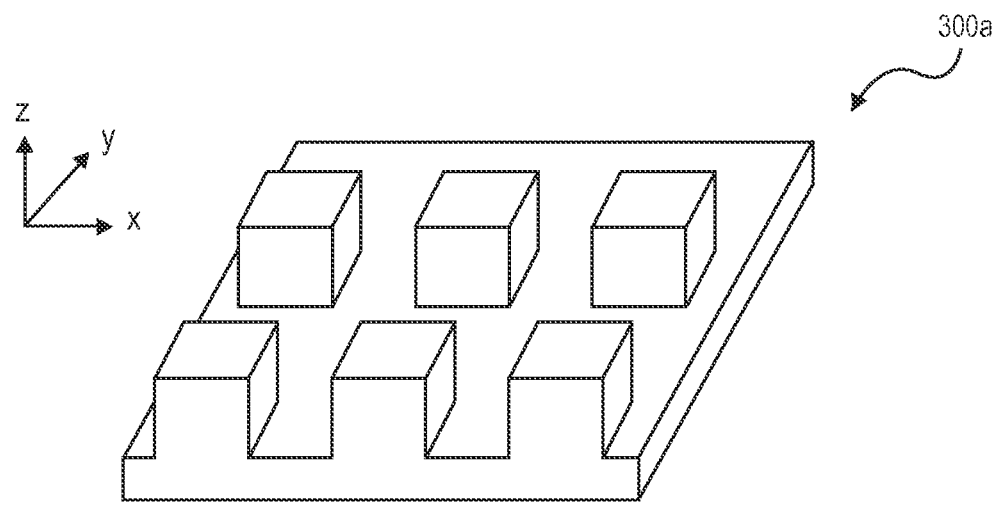
FIG. 3A illustrates an exemplary diffracting structure including a periodic grating with a profile that varies in the x-y plane, in accordance with an embodiment of the invention.
Figure 3B:
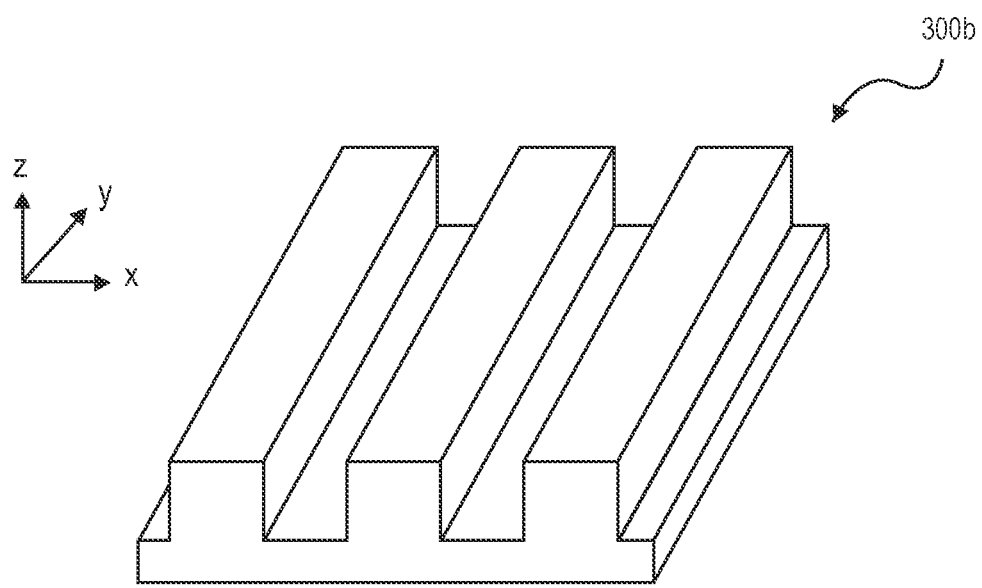
FIG. 3B illustrates an exemplary diffracting structure including a periodic grating with a profile that varies in the x-direction but not in the y-direction, in accordance with an embodiment of the invention.

The method 150 begins at block 152 with an optical metrology system performing measurements of a sample with a diffracting structure. Performing measurements involves shining light or other electromagnetic radiation on the sample and measuring spectral information for the sample such as reflectance. For example, the method may involve illuminating or irradiating the sample with any optical or non-optical electromagnetic waves, such as infrared radiation, visible-spectrum radiation, ultraviolet (UV) radiation, extreme ultraviolet (EUV) radiation, x-ray radiation, or any other electromagnetic radiation. The diffracting structure being evaluated can include a grating, such as the periodic diffracting structures 300a of FIG. 3A and 300b of FIG. 3B, or non-periodic diffracting structures such as the sample 400 of FIG. 4. FIGS. 3A and 3B illustrate periodic gratings 300a and 300b that may include patterned metal, and/or non-metal lines, according to embodiments.

FIG. 3A illustrates an "island grating" 300a, which is periodic in two dimensions. The periodic grating 300a has a profile that varies in the x-y plane. The periodic grating 300a is also symmetric in two dimensions (here, in the x- and y-dimensions). A grating is symmetric in a dimension if the grating is the same on either side of a symmetry plane. For example, a grating is symmetric in the x-dimension if the grating is the same on either side of a plane defined by x=constant. FIG. 3B illustrates a periodic grating having a profile that varies in the x-direction but not in the y-direction. Thus, periodic grating 300b is periodic in one dimension.

The sample 400 of FIG. 4 includes a non-periodic grating, and is described in more detail below with respect to the method 200 of FIG. 2.

Returning to FIG. 1B, at block 154, the optical metrology system identifies or provides an initial model of the measurement process. Providing the initial model of the measurement process includes constructing a geometric model of the diffracting structure, determining how to parameterize the geometric model, characterizing the incident light, and characterizing the optical measurement system. Typically, model parameters include: CDs, SWAs and HTs of gratings, material dispersion parameters, layer thicknesses, angle of incidence of light directed onto the diffracting structure, calibration parameters of the optical measurement system, and/or any other parameters that may affect polarization and intensity of the light reflected from or transmitted through a material.

Based on the model parameters, the optical metrology system computes spectral information for the model at block 156. Computing spectral information can include, for example, determining reflectance from the diffracting structure via a simulation.

At block 158, the optical metrology system attempts to fit the modeled data obtained at block 156 to the measured data obtained at block 152. Fitting the modeled data generally involves comparing the modeled data to the measured data and determining an error between the two sets of data. At block 160, the optical metrology system determines whether the model is a good fit. According to one embodiment, the model is a good fit if the error between the modeled data and the measured data is less than a predetermined value. If the model is a good fit, the optical metrology system determines a characteristic of the diffracting structure at block 164. If the model is not a good fit, the optical metrology system determines if any other termination conditions have occurred at block 161. Termination conditions can include, for example: reaching a maximum number of iterations, determining that the difference between the previous model parameters and current model parameters is less than a threshold value, and/or any other conditions justifying discontinuing further model iterations. If a termination condition is not met, the optical metrology system adjusts the model parameters at block 162, and repeats the operations at blocks 156-160. The initial model identified is generally based on expected parameters of the diffracting structure, and typically results in an error significant enough to require additional iterations of blocks 156-160.

Upon completing multiple iterations of blocks 156-160, the scatterometry model is typically close enough to the actual diffracting structure that determining characteristics of the actual diffracting structure at block 164 may simply involve ascertaining the best fit model parameters. This can be true, for example, for geometric parameters that have a one-to-one correspondence with a single parameter used in the scatterometry model. Determining other parameters of the actual diffracting structure may involve additional operations such as adding two parameters of the scatterometry model together.

The above-described method 150 of FIG. 1B is a general method for evaluating a diffracting structure in accordance with an embodiment of the invention. FIG. 2 is a flow diagram illustrating a specific example of a method for evaluating a diffracting structure. Like the method 150 of FIG. 1B, the method of FIG. 2 may be performed by an optical metrology system such as the systems described with respect to FIG. 1A.

Figure 2:
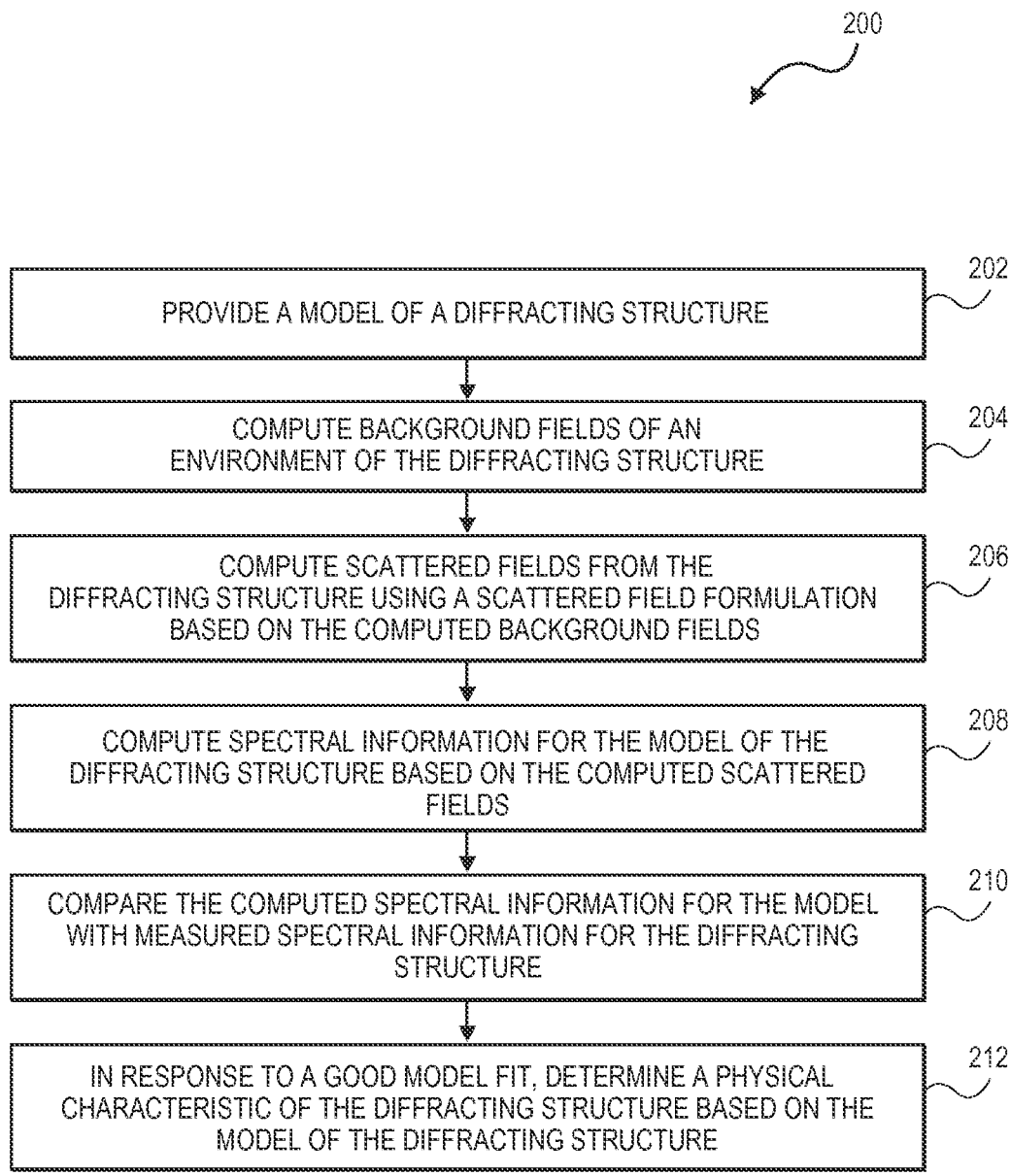
FIG. 2 is a flow diagram illustrating a method for evaluating a diffracting structure, in accordance with an embodiment of the invention.

FIG. 2 illustrates an exemplary method 200 for evaluating a diffracting structure, in accordance with an embodiment of the invention. As is explained in more detail below, embodiments involve separating the total field into two parts: background fields and scattered fields. The illumination field may be obtained by summing up the constituent plane waves (e.g., pupil sampling) coherently, and the background field may be obtained using the principle of superposition. The total scattering field under illumination of arbitrary NA and arbitrary profile may then be computed in one simulation.

The method 200 begins at block 202 with the optical metrology system providing a model of the diffracting structure. As mentioned above, providing a model may include constructing a geometric model of the diffracting structure and determining how to parameterize the geometric model. Determining how to parameterize the model may include determining which parameters to fix (e.g., hold constant), determining which parameters to float (e.g., determining which variables to keep as variables or unknowns in the model), and determining values for fixed parameters for a given simulation.

Figure 8A:
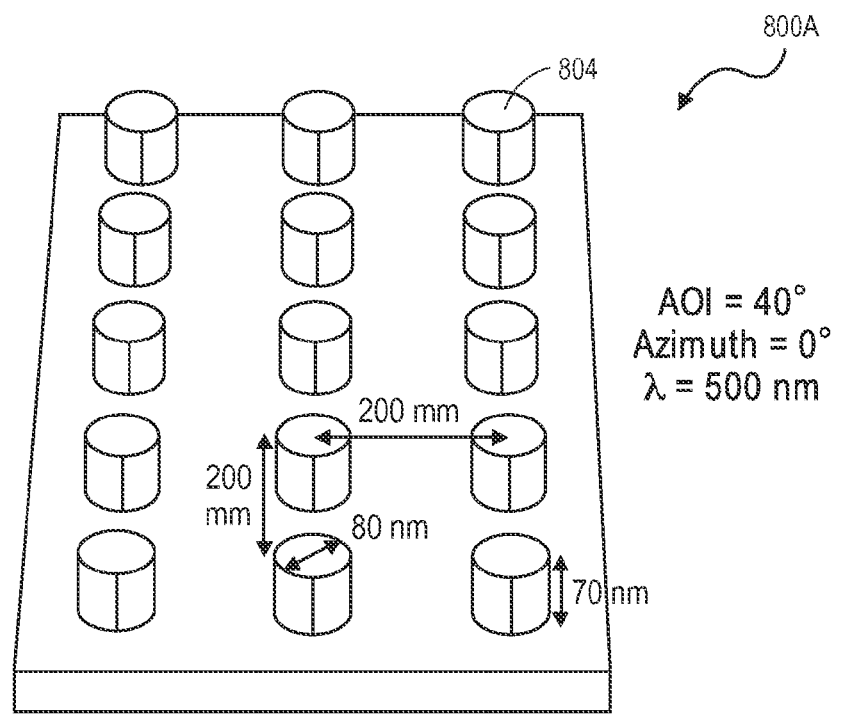
FIG. 8A illustrates an isometric view of an exemplary diffracting structure including posts, in accordance with embodiment herein.
Figure 8B:
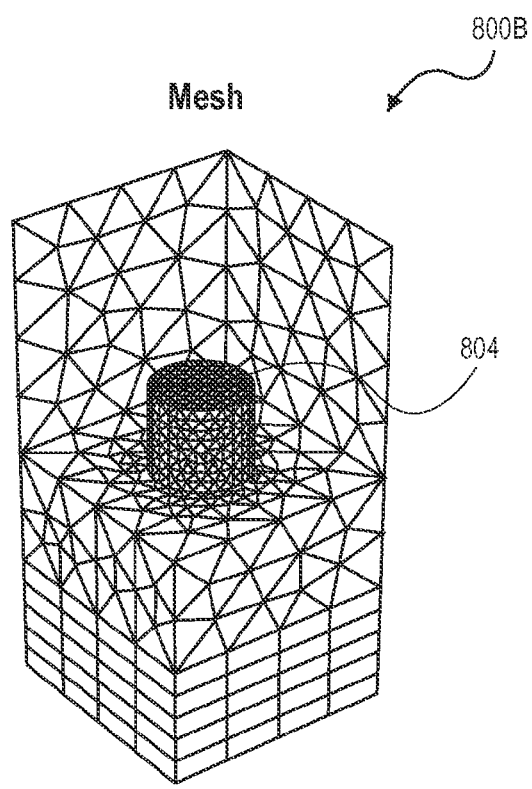
FIG. 8B illustrates a model of a post of the diffracting structure of FIG. 8A discretized using a mesh, in accordance with embodiment herein.

In one embodiment, providing the model of the diffracting structure involves discretizing the diffracting structure into a mesh. For example, FIG. 8A illustrates an isometric view of an exemplary sample 800A including posts 804, and FIG. 8B illustrates a model 800B of one of the posts 804 that has been discretized using a mesh, in accordance with an embodiment. The generated mesh may strongly influence the computational speed, system memory usage, and the accuracy of the solution. Therefore, embodiments may involve mesh optimizations to improve speed, memory usage, or solution accuracy. For example, discretizing the diffracting structure model into the mesh may involve refining the mesh in areas of interest such as, for example: a defect, areas with line edge roughness, high field gradients, or fine features. Such mesh optimizations may especially benefit models of finite structures because the domain size is typically significantly larger in comparison to models with periodic structures.

The method of discretizing the diffracting structure may influence not only the accuracy of functions and computations for determining spectral information, but also the derivatives of the functions. Function derivatives may include, for example, derivatives with respect to system parameters, spatial coordinates, structural parameters, or other parameters used in the model. Smooth (e.g., continuously changing) derivatives may be required for some embodiments. For example, in one embodiment involving a regression analysis (e.g., a regression analysis for library generation, inverse scatterometry, or for a sensitivity analysis), smooth derivatives may be important.

According to an embodiment, smooth derivatives may be obtained using a deformed mesh method. In a deformed mesh method, subsequent model iterations involve scaling or deforming the mesh. In contrast to existing methods, such as "automeshing," in which a new mesh is generated for each different simulation (also known as "re-meshing"), a deformed mesh approach involves changing a mesh continuously between several points for different simulations. For example, the mesh can change continuously between several points where a finite-difference derivative is computed. Changing the mesh continuously between several points may involve scaling the mesh along the direction normal to the moving surface. Scaling the mesh instead of generating a new mesh preserves the topography of the mesh between different simulations, and therefore can provide smooth derivatives.

Figure 9A:
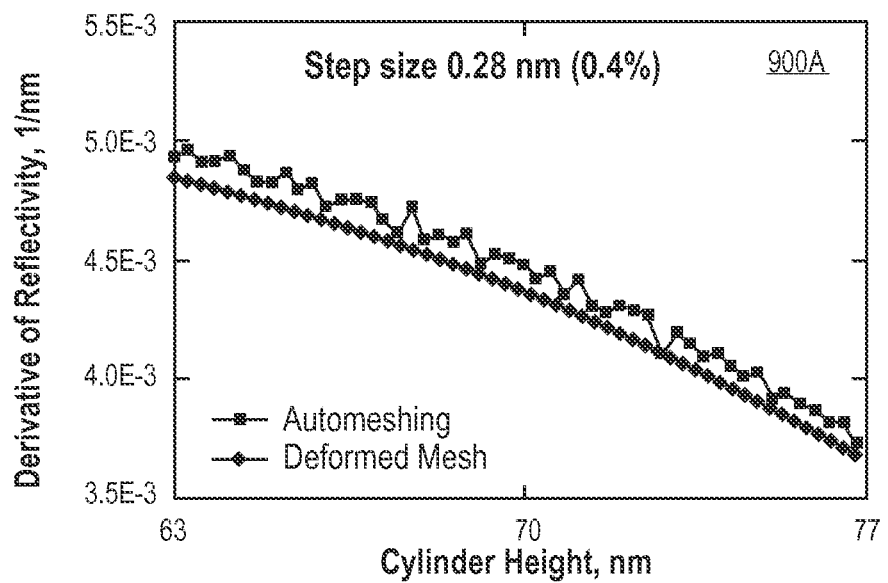
FIGS. 9A and 9B illustrate derivatives of reflectivity as a function of height of a post using different methods of meshing with different step sizes in post height, in accordance with embodiments herein.
Figure 9B:
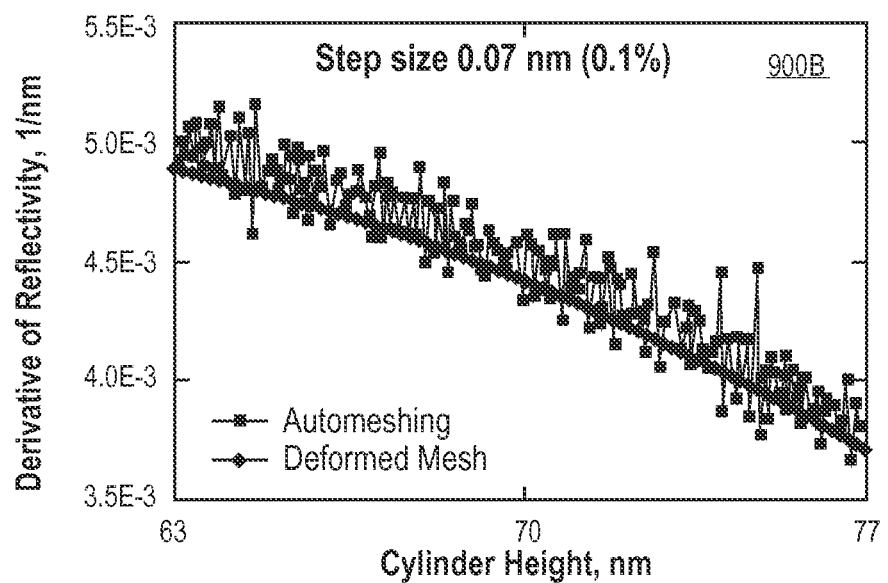

FIGS. 9A and 9B illustrate graphs of derivatives of reflectivity as a function of height of a post using different methods of meshing with different step sizes in post height, in accordance with embodiments herein. The derivatives in the graphs 900A and 900B of FIGS. 9A and 9B were computed as the change in reflectivity divided by the step size, as in equation (1):

$$\frac{\partial R}{\partial Ht} = \frac{\Delta R}{\Delta Ht} \quad (1)$$

where R is the reflectivity, and Ht is the height of the modeled post. As can be seen from graphs 900A and 900B, the automeshing method does not result in a smooth derivative. In contrast, the deformed mesh method results in a smooth derivative independent of step size. Hence, the derivative using the deformed mesh method may be considered as an analytical derivative.

Returning to the method 200 of FIG. 2, at block 204, the method involves computing the background electric or magnetic fields of an environment of the diffracting structure. The "environment" of the diffracting structure could be, for example, free space, or one or more films disposed under the diffracting structure. The "background field" is the field in the absence of the diffracting structure (scatterer). In an example where the background is assumed to be free space, computing the background electric or magnetic fields of the environment may involve computing electric or magnetic fields for free space without considering the effects of the diffracting structure. In an example where the background is assumed to be a film, or film stack (e.g., one or more films or layers), the method involves computing electric or magnetic fields of the one or more films disposed under the diffracting structure without considering the effects of the diffracting structure. FIG. 4 illustrates a cross-sectional view of an exemplary non-periodic diffracting structure disposed on a multi-layer substrate background, in accordance with an embodiment of the invention. In FIG. 4, a sample 400 includes a substrate 406 over which a film 404 is disposed. A non-periodic grating 402 is disposed over the film 404. In one example, the substrate 406 is a silicon substrate over which a $SiO_2$ film 404 was formed, and silicon bars 402 were formed over the $SiO_2$ film 404. Computing the background fields for the sample 400 may involve, for example, computing the fields for air in the absence of the substrate 406, film 404, and grating 402. In another example, computing the background fields for the sample 400 may involve computing the fields for the substrate 406 and/or the film 404 in the absence of the grating 402.

Figure 4:
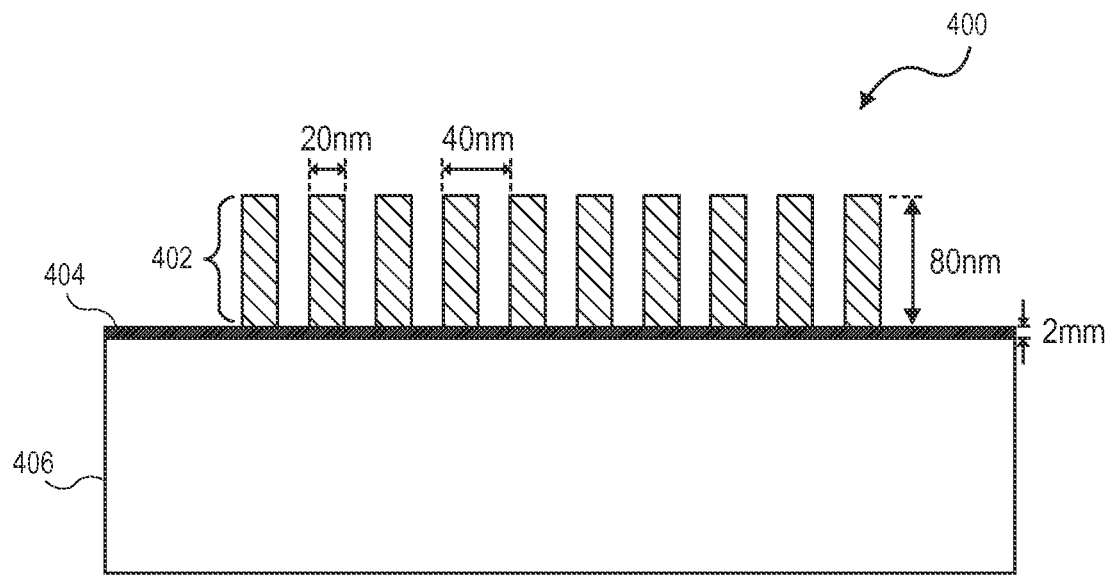
FIG. 4 illustrates a cross-sectional view of an exemplary non-periodic diffracting structure disposed on a multi-layer substrate, in accordance with an embodiment of the invention.

FIG. 4 illustrates a grating with ten lines, however, the methods described herein may also be performed for other finite structures with other dimensions. For Fourier solvers (e.g., RCWA solvers), the number of lines in a grating will generally impact the accuracy of the simulated results, where a larger number of lines yields more accurate spectral information. In contrast, embodiments of the invention enable accurate solutions for even small numbers of lines. Simulations for gratings with different numbers of lines were performed, as is described in more detail below with respect to FIGS. 7A and 7B.

Figure 5:
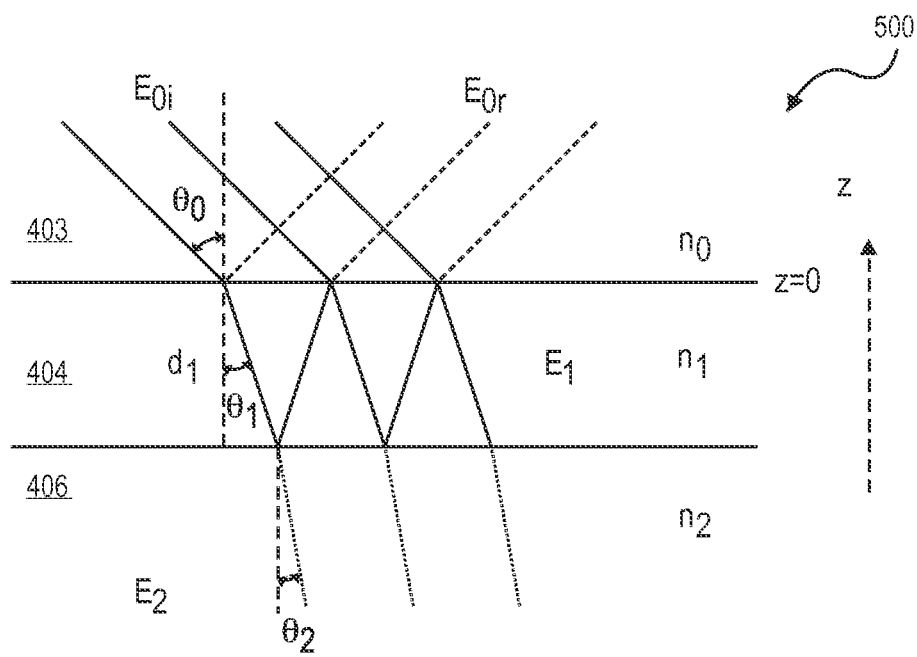
FIG. 5 illustrates background field beams for a multi-layer film stack, such as in FIG. 4, in accordance with an embodiment of the invention.

FIG. 5 illustrates background field beams 500 for a multi-layer film stack, such as in FIG. 4, in accordance with an embodiment of the invention. According to an embodiment, the background field is a superposition of incident and reflected fields in a top medium, upward and downward waves in each intermediate layer, and the transmitted wave in the bottom substrate. In the illustrated example, the top medium $n_0$ is the air 403 above the film 404, the intermediate layer $n_1$ is the film 404, and the bottom substrate $n_2$ is the substrate 406. The top air layer and bottom substrate may be assumed to go to infinity. In one example, assuming a one-layer thin film, for an arbitrary incident plane wave:

Incident + Reflected
$$E_0 = E_{0i} + E_{0r} \qquad (2)$$
$$= A_0 e^{-j(k_{0x}x + k_{0y}y + k_{0z}z)} + R A_0 e^{-j(k_{0x}x + k_{0y}y - k_{0z}z)}$$

Thin film
$$E_1 = E_{1d} + E_{1u} \qquad (3)$$
$$= C_d A_0 e^{-j(k_{1x}x + k_{1y}y + k_{1z}z)} + C_u A_0 e^{-j(k_{1x}x + k_{1y}y - k_{1z}z)}$$

Transmitted
$$E_2 = T A_0 e^{-j(k_{2x}x + k_{2y}y + k_{2z}(z+d_1))} \qquad (4)$$

Reflection Coefficient
$$R = \frac{r_{01} + r_{12} e^{-j2\beta}}{1 + r_{01} r_{12} e^{-j2\beta}} \qquad (5)$$

"Up" Wave
$$C_u = \frac{t_{01} r_{12} e^{-j2\beta}}{1 + r_{01} r_{12} e^{-j2\beta}} \qquad (6)$$

"Down" Wave
$$C_d = \frac{t_{01}}{1 + r_{01} r_{12} e^{-j2\beta}} \qquad (7)$$

Transmission Coefficient
$$T = \frac{t_{01} + t_{12} e^{-j2\beta}}{1 + r_{01} r_{12} e^{-j2\beta}} \qquad (8)$$

Phase Delay Constant
$$\beta = \frac{2\pi}{\lambda} n_1 d_1 \cos\theta_1 \qquad (9)$$

Interface Coefficient, s-polarization
$$r_{abs} = \frac{n_a \cos\theta_a - n_b \cos\theta_b}{n_a \cos\theta_a + n_b \cos\theta_b}, \qquad (10)$$
$$t_{mns} = \frac{2 n_a \cos\theta_a}{n_a \cos\theta_a + n_b \cos\theta_b}$$

Interface Coefficient, p-polarization
$$r_{mnp} = \frac{n_b \cos\theta_a - n_a \cos\theta_b}{n_b \cos\theta_a + n_a \cos\theta_b}, \qquad (11)$$
$$t_{mns} = \frac{2 n_a \cos\theta_a}{n_b \cos\theta_a + n_a \cos\theta_b}$$

Returning to operation 204 of FIG. 2, the background fields may be represented with Maxwell's equations. For time-harmonic (e.g., monochromatic) background electric fields, Maxwell's equations result in equation (12):

$$\nabla \times \left( \frac{1}{\tilde{\mu}} \nabla \times \vec{E}_b \right) - k_0^2 \tilde{\varepsilon} \vec{E}_b = 0 \qquad (12)$$

where $\vec{E}_b$ is the background electric field and $\tilde{\varepsilon}$ and $\tilde{\mu}$ represent the relative permittivity and permeability in the absence of the scatterer.

In one embodiment, computing the background electric or magnetic fields at a given point involves decomposing modeled incident illumination into a set of plane waves. Decomposing the modeled incident illumination into the set of plane waves may involve a discrete decomposition or a continuous decomposition. For example, numerical simulations may use the discrete decomposition given in equation (13):

$$\vec{E}(\vec{r}_0) = \sum_{\vec{k}} \vec{E}(\vec{k}) e^{-i\vec{k}\cdot\vec{r}_0} \qquad (13)$$

To compute the background field at a given point in space $r(x, y, z)$, the set of plane waves are then propagated from a predetermined initial point in space $r_0$ $(x_0, y_0, z_0)$ to that given point, r. According to an embodiment, the background field is computed in the absence of the scatterers. The method then involves re-constructing the fields from the collection of the plane waves at the point r. Re-constructing the fields may involve summing the propagated set of plane waves at the given point r, for example, according to equation (14):

$$\vec{E}(\vec{k}) = \sum_{\vec{r}} \vec{E}(\vec{r}) e^{-i\vec{k}\cdot\vec{r}} \qquad (14)$$

In reality, the fields are continuous through the angle of incidence, but in equations (12) and (13), the fields are assumed to be a sum of different angles or k vectors. Although a similar assumption may be made in some conventional methods, conventional methods compute the fields for each angle of incidence (e.g., perform a simulation for each angle of incidence). In contrast, embodiments enable computing the fields for all the angles of incidence at once (e.g., with one simulation).

At block 206, the method involves computing scattered electric or magnetic fields from the diffracting structure using a scattered field formulation based on the computed background fields. The "scattered field" is the response of the scatterer to the background field. The "scatterer" is the diffracting structure that was not considered when computing the background field. In an example where the background fields were computed for free space, the scattered fields may consider the presence of a grating as well as one or more layers disposed under the grating. For example, referring to FIG. 4, the scattered fields may consider the grating 402 as well as the film 404 and the substrate 406. In an example where the background fields were computed for one or more layers disposed under a grating, the scattered fields may consider the presence of the grating disposed over those layers. For example, if the background fields consider the substrate 406 and/or the film 404, but not the grating 402, the scattered fields may consider the grating 402. According to one embodiment, computing the scattered fields involves solving for equations (15)-(17) below.

After accounting for the scatterer, the electric fields can be expressed as equation (15):

$$\vec{E} = \vec{E}_b + \vec{E}_S \qquad (15)$$

where $\vec{E}$ is the electric field for the full structure, and $\vec{E}_S$ is the scattered electric field, so that:

$$\nabla \times \left(\frac{1}{\tilde{\mu}} \nabla \times \vec{E}_b\right) - k_0^2 \tilde{\varepsilon} \vec{E}_b = 0 \qquad (16)$$

where $\epsilon$ and $\mu$ represent the actual material properties including the scatterer.

The scattered field $\vec{E}_S$ is then given by equation (17):

$$\nabla \times \left(\frac{1}{\tilde{\mu}} \nabla \times \vec{E}_s\right) - k_0^2 \tilde{\varepsilon} \vec{E}_s = \nabla \times \left(\left(\frac{1}{\tilde{\mu}} - \frac{1}{\mu}\right) \nabla \times \vec{E}_b\right) - k_0^2 (\tilde{\varepsilon} - \varepsilon) \vec{E}_b \qquad (17)$$

where $\vec{E}_S$ results from the excitation by the background field $\vec{E}_b$ of the "inserted" scatterer. The background field $\vec{E}_b$ may be arbitrary as long as it satisfies the time-harmonic equation involving $\epsilon$ and $\mu$. For linear materials (e.g., for materials where $\epsilon$ and $\mu$ are independent of $\vec{E}$), the principle of superposition applies. For non-magnetic materials, $\mu$ can be assumed to be 1 and equation (17) can be simplified as in equation (18):

$$\nabla \times \nabla \times \vec{E}_S + k_0^2 n^2 \vec{E}_S = k_0^2 (\tilde{n}^2 - n^2) \vec{E}_b \qquad (18)$$

where n is a complex index of refraction. In the case of non-magnetic materials, $\epsilon = n^2$.

The set of Maxwell's equations (e.g., equations (12) and (17)) may be solved using any spatial solver (e.g., a finite element method, method of moments, finite-difference time domain method, etc.), or any other method for solving Maxwell's equations. At block 208, the scattered fields together with the background fields allow for computation of reflectivity (or other spectral information) for the specified incident illumination.

In contrast to existing methods, embodiments do not require periodic boundary conditions. The scattered field formulation may be used in conjunction with perfectly matching layers (PML) instead of boundary conditions (BC). According to embodiments, the use of PML involves an artificial domain surrounding the domain of interest to absorb the outgoing waves without reflection. The absorption may be done, for example, through careful introduction of artificial dissipative materials, or through coordinate transformation (e.g., real/complex coordinate stretching). Therefore, embodiments enable modeling periodic as well as non-periodic and isolated structures. The ability to model isolated structures may be especially beneficial in applications such as inspection, where defects are typically localized and not periodic. However, the use of PML may involve additional computational costs. In other embodiments, other types of boundary conditions (e.g., scattering boundary conditions) may be applied. For example, radiation boundary conditions involve a boundary that is transparent, but only to specific types of outgoing waves. In one such embodiment involving radiation boundary conditions, no extra domains are required.

Additionally, using non-periodic boundary conditions may enable the use of plane-wave incident illumination as well as finite beam illumination. Therefore, the electric field $\vec{E}(\vec{K})$ resulting from incident illumination (e.g., in equation (14)) may be chosen in such a way that it accurately represents the actual measurement device's illumination, in contrast to existing methods which typically use a plane-wave simplification. Embodiments may also enable modeling of arbitrary illumination and complex optical systems (e.g., "apodized" objectives), and enable optimization of the incident illumination and optical systems to have desired properties (e.g., desired box size).

According to embodiments, the described methods may also enable the unique capability of light scatter computations using coherent and partially-coherent illumination beams. Because certain optical effects (e.g., speckle) arise from an interference of wave fronts, proper description of coherence may be necessary for modeling such a system, and may be especially beneficial in laser-based scatterometers. Coherent effects may contribute in the reflection patterns from structures with random scatterers. For example, accurately modeling roughness effects (e.g., line edge roughness, line width roughness, and other roughness effects), a coherent or partially-coherent illumination model may be required. In contrast to existing methods, embodiments enable modeling of such coherent or partially-coherent illumination beams.

Furthermore, according to embodiments, because the scattered fields include all the information about the diffraction from the structure, reflectivity of all diffraction orders may be computed in one simulation. Additionally, in one embodiment, computing the spectral information may involve computing specular reflection and non-zero diffraction orders at once. As mentioned above, embodiments may also enable computing the background and scattered fields for multiple angles of incidence at once. Therefore, embodiments may provide significant improvements in computational speed over existing methods, which typically require one simulation for each angle of incidence.

At block 210, the method involves comparing the computed spectral information for the model with measured spectral information for the diffracting structure. At block 212, in response to a good model fit, the method involves determining a physical characteristic of the diffracting structure based on the model of the diffracting structure.

Thus, an optical metrology system can use the methods described above with respect to FIGS. 1B and 2 to evaluate a diffracting structure.

According to one embodiment, the above-described method may be used in conjunction with existing methods such as Fourier-space methods. For example, in an embodiment where the diffracting structure includes both a periodic region and a non-periodic region, computing the background fields of the environment may involve computing fields of the periodic region using RCWA, and computing fields of the non-periodic region using the method 200 of FIG. 2 using the scattered field formulation based on the computed background fields. A final solution for the structure (e.g., in the form of reflectance or other spectral information), may then be obtained by applying domain decomposition to the fields for the periodic and non-periodic regions. Such a hybrid method would enable improved computational speed for the periodic regions while preserving the ability to model non-periodic and isolated targets. Therefore, such hybrid methods may provide significant improvement in computational speed when analyzing numerically expensive structures such as large-pitch gratings, high aspect ratio structures, through-silicon vias, etc.

In one embodiment, other non-diffraction modeling may be performed using the above-described methods instead or, or in addition to, modeling to obtain spectral information. For example, methods may involve performing microstress analysis or process simulations using the computed scattered fields described above.

Figure 6A:
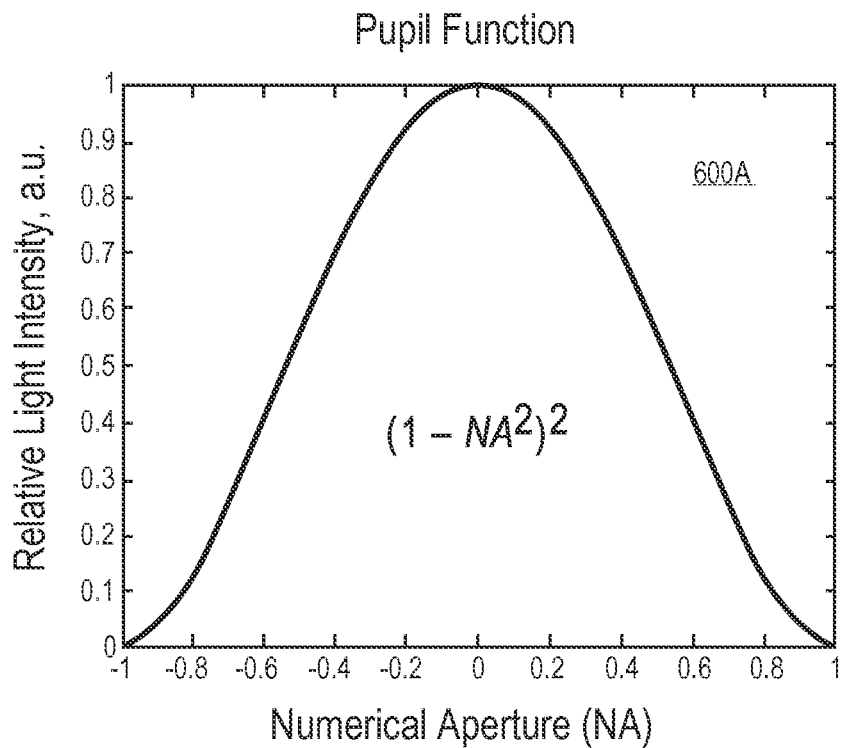
FIG. 6A illustrates a pupil function for modeled incident illumination, in accordance with an embodiment of the invention.

FIGS. 6A-6C, 7A, and 7B illustrate examples of simulations using methods described herein. FIG. 6A illustrates a pupil function of modeled incident illumination, in accordance with an embodiment of the invention. The graph 600A illustrates illumination vs. numerical aperture (NA) based on the pupil function in equation (19):

$$(1-NA^2)^2 \qquad (19)$$

Figure 6B:
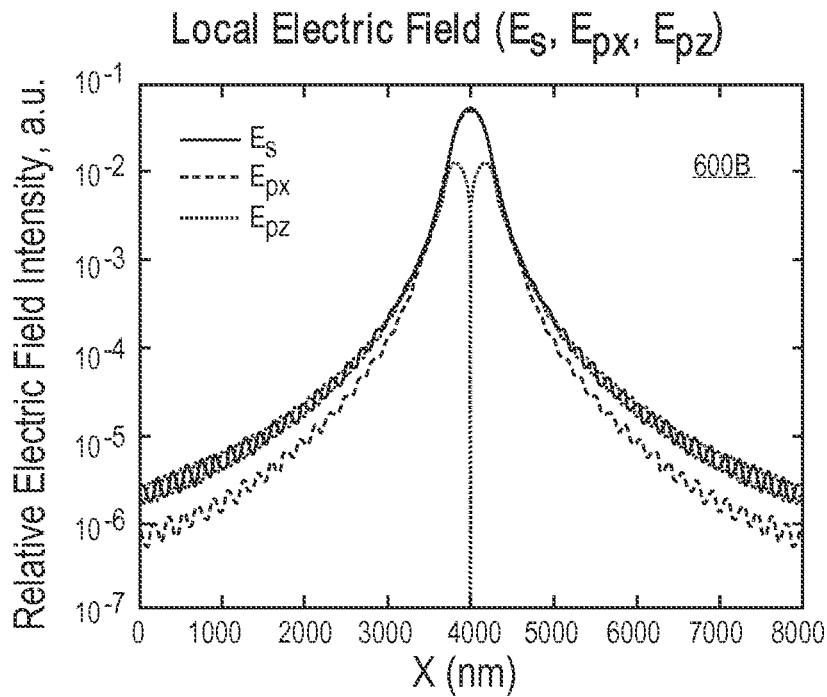
FIG. 6B illustrates a graph of the local electric field at different points of a diffracting structure, in accordance with an embodiment of the invention.

FIG. 6B illustrates a graph 600B of the local electric field resulting from the incident illumination at different points of a diffracting structure, in accordance with an embodiment of the invention. The graphs 600A and 600B show that the simulations are done for finite beams (e.g., using "spot" illumination), not plane waves. In spot illumination, most of the light falls on one line or other feature. The graphs 600A and 600B also show that the pupil function has a sizeable signal at NA=0.85 and good localization in x-space.

Figure 6C:
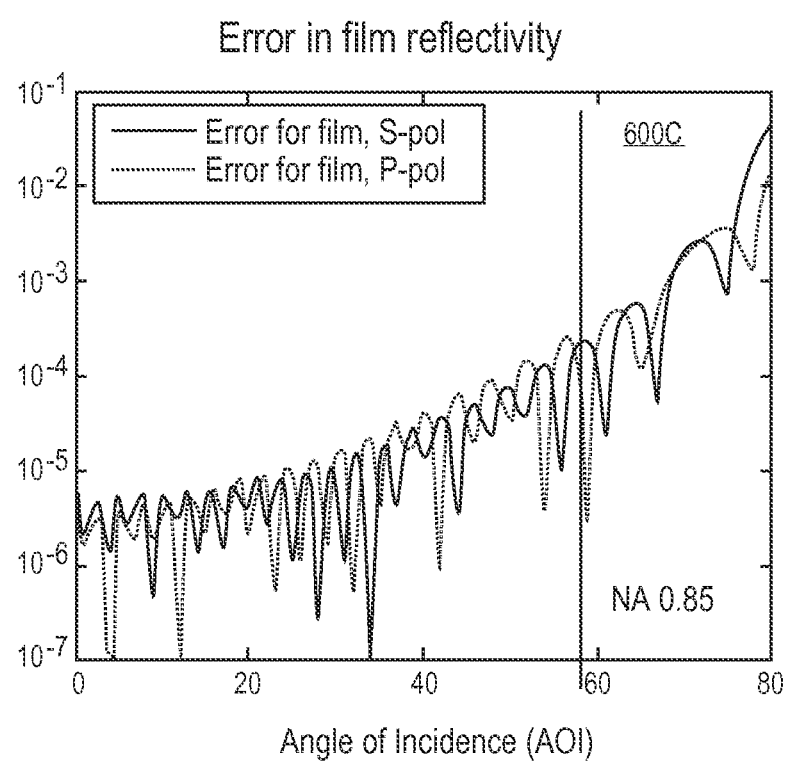
FIG. 6C illustrates a graph of the error in film reflectivity, in accordance with an embodiment of the invention.

FIG. 6C illustrates a graph of the error in film reflectivity, in accordance with an embodiment of the invention. Simulations were performed on structures without gratings, such as the layers 406 and 404 in FIG. 4, to obtain computed reflectance values from the structure. The reflectance was then computed using an analytical method. The reflectance computed by the simulation and the analytical method were compared to estimate the error in the reflectance obtained by the simulation with a finite domain size, as illustrated in the graph 600C. The graph 600C illustrates the estimated error for angles of incidence between 0 and 80 degrees for S- and P-polarization. As can be seen in the graph 600C, the error is below $10^{-5}$ for a small NA, and goes up to $10^{-4}$ for 0.85 NA.

However, even for NA=0.85, the error is small, which shows the described methods provide accurate spectral information for evaluation of a diffracting structure.

Figure 7A:
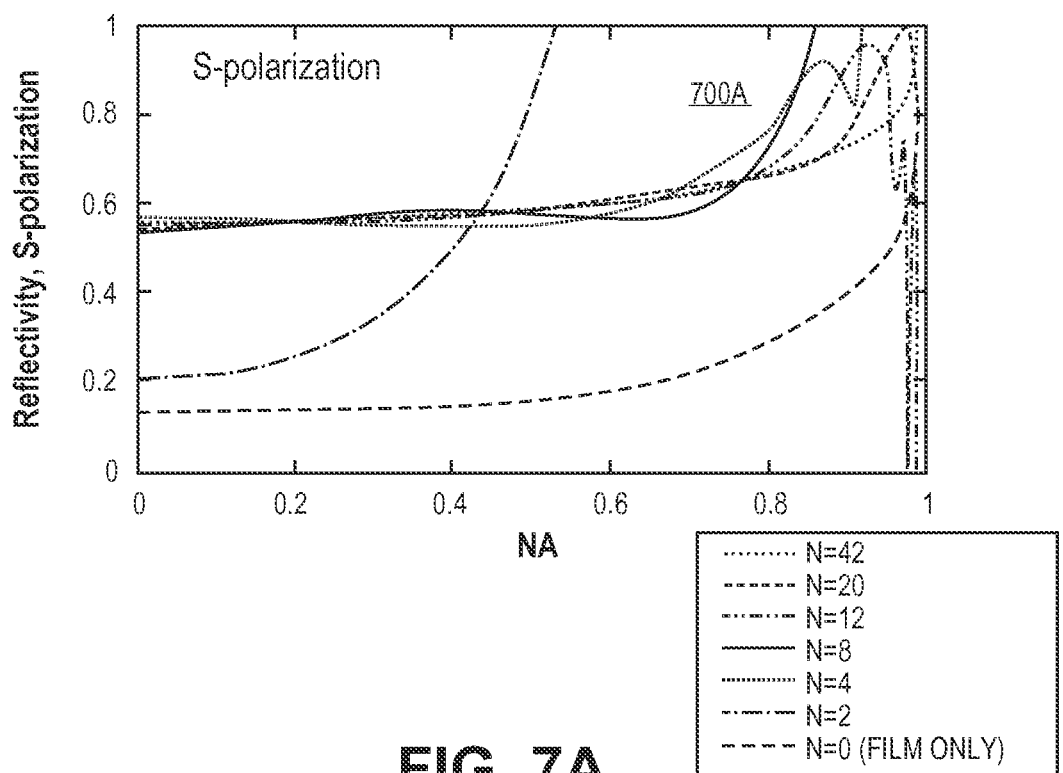
FIGS. 7A and 7B illustrate graphs of reflectivity as a function of numerical aperture for diffracting structures with different numbers of lines, in accordance with embodiment herein.
Figure 7B:
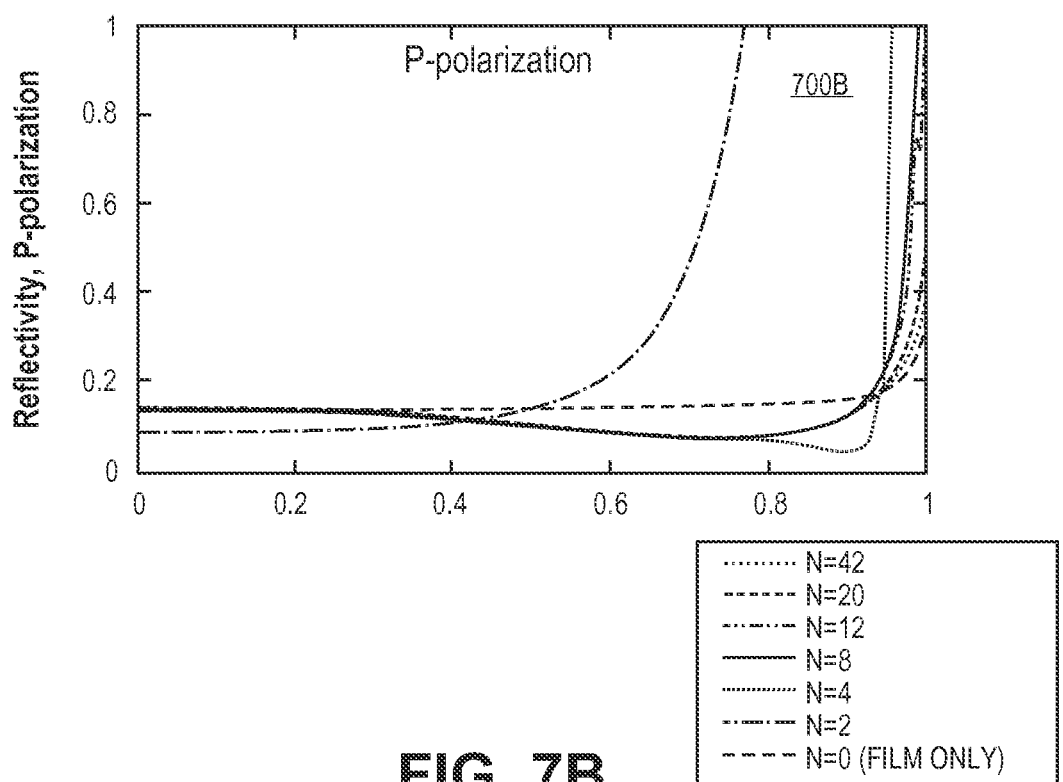

FIGS. 7A and 7B illustrate graphs of reflectivity as a function of numerical aperture for diffracting structures with different numbers of lines, in accordance with embodiment herein. The graph 700A of FIG. 7A illustrates reflectivity with S-polarization, while the graph 700B of FIG. 7B illustrates reflectivity with P-polarization. Simulations were performed starting with 42 lines (for a grating having a width of about 10 μm at a 240 nm pitch), down to 2 lines. The error for the grating with 42 lines was well below $10^{-4}$, and therefore sufficient to be considered as "infinite." Gratings with numbers of lines down to 4 were still relatively close to "infinity." However, gratings with two lines resulted in significantly different reflectivity. Also of note is that the reflectivity change for S-polarization was larger than for P-polarization.

Figure 10:
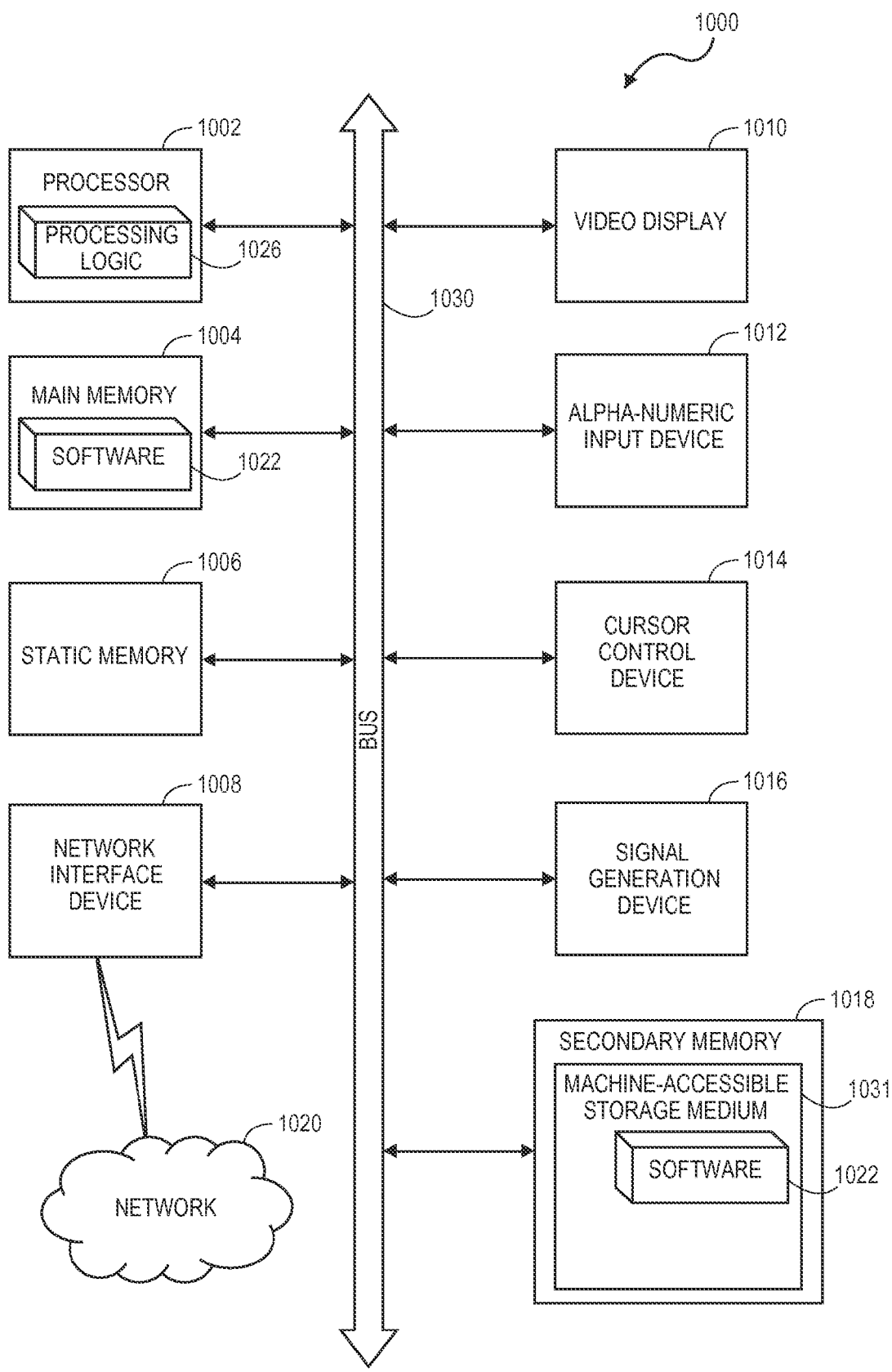
FIG. 10 is a block diagram of an exemplary computing system in accordance with which embodiments may operate, be installed, integrated, or configured.

FIG. 10 illustrates a block diagram of an exemplary computing system in accordance with which embodiments may operate, be installed, integrated, or configured. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a server, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computing system 1000 includes a processor 1002, a main memory 1004 (e.g., read-only memory (ROM), flash memory, dynamic random access memory (DRAM) such as synchronous DRAM (SDRAM) or Rambus DRAM (RDRAM), etc.), a static memory 1006 (e.g., flash memory, static random access memory (SRAM), etc.), and a secondary memory 1018 (e.g., a data storage device), which communicate with each other via a bus 1030.

Processor 1002 represents one or more general-purpose processing devices such as a microprocessor, central processing unit, or the like. More particularly, the processor 1002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1002 may also be one or more special-purpose processing devices such as an application specific integrated circuit (ASIC), a field programmable gate array (FPGA), a digital signal processor (DSP), network processor, or the like. Processor 1002 is configured to execute the processing logic 1026 for performing the operations and steps discussed herein.

The computing system 1000 may further include a network interface device 1008. The computing system 1000 also may include a video display unit 1010 (e.g., a liquid crystal display (LCD) or a cathode ray tube (CRT)), an alphanumeric input device 1012 (e.g., a keyboard), a cursor control device 1014 (e.g., a mouse), and a signal generation device 1016 (e.g., a speaker).

The secondary memory 1018 may include a machine-accessible storage medium (or more specifically a computerreadable storage medium) 1031 on which is stored one or more sets of instructions (e.g., software 1022) embodying any one or more of the methodologies or functions described herein. The software 1022 may also reside, completely or at least partially, within the main memory 1004 and/or within the processor 1002 during execution thereof by the computing system 1000, the main memory 1004 and the processor 1002 also constituting machine-readable storage media. The software 1022 may further be transmitted or received over a network 1020 via the network interface device 1008.

While the machine-accessible storage medium 1031 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media, as well as other similarly non-transitory media.

Figure 11:
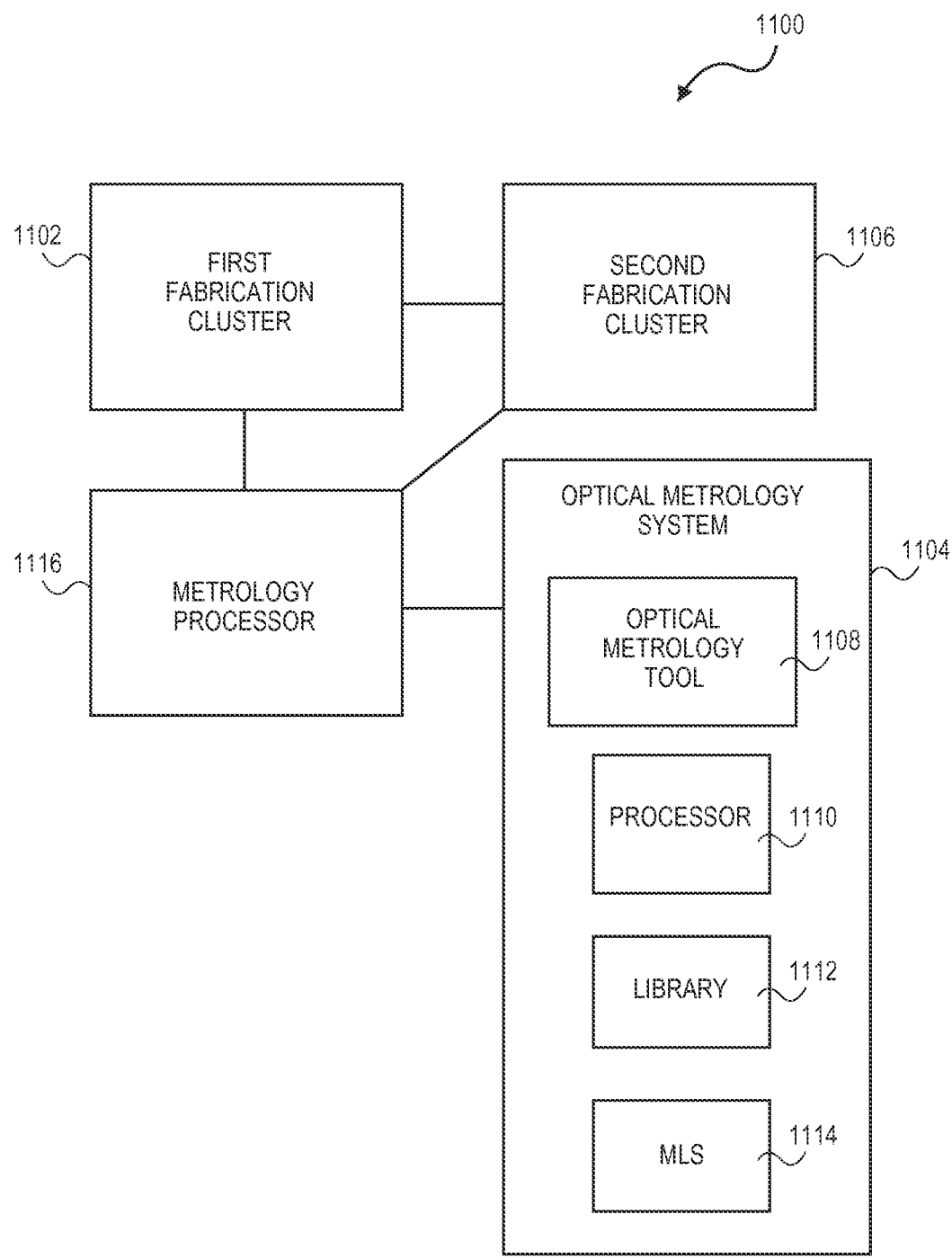
FIG. 11 is a block diagram illustrating select elements of a system according to an embodiment for determining and utilizing profile parameters for automated process and equipment control.

FIG. 11 is an exemplary block diagram of a system for determining and utilizing profile parameters for automated process and equipment control.

System 1100 includes a first fabrication cluster 1102 and an optical metrology system 1104 (e.g., an optical measurement system). The optical metrology system 1104 can include, for example, a spectroscopic ellipsometer (SE), a dual-beam spectrophotometer (DBS), a polarized DBS, a beam reflectometer, or any other optical measurement system. System 1100 also includes a second fabrication cluster 1106. Although the second fabrication cluster 1106 is depicted in FIG. 11 as being subsequent to the first fabrication cluster 1102, it should be recognized that the second fabrication cluster 1106 can be located prior to the first fabrication cluster 1102 in the system 1100 (e.g. and in the manufacturing process flow).

A photolithographic process, such as exposing and/or developing a photoresist layer applied to a wafer, can be performed using the first fabrication cluster 1102. In one exemplary embodiment, the optical metrology system 1104 includes an optical metrology tool 1108 and a processor 1110. The optical metrology tool 1108 is configured to measure a diffraction signal off of the structure. Thus, the optical metrology system 1104 includes logic to receive measured spectral information for a diffracting structure. If the measured diffraction signal and the simulated diffraction signal match, one or more values of the profile parameters are presumed equal to the one or more values of the profile parameters associated with the simulated diffraction signal.

In one exemplary embodiment, the optical metrology system 1104 can also include a library 1112 with a plurality of simulated (e.g., computed) diffraction signals and a plurality of values of one or more profile parameters associated with the plurality of simulated diffraction signals. The library can be generated in advance. The processor 1110 can compare a measured diffraction signal of a structure to the plurality of simulated diffraction signals in the library. When a matching simulated diffraction signal is found, the one or more values of the profile parameters associated with the matching simulated diffraction signal in the library is assumed to be the one or more values of the profile parameters used in the wafer application to fabricate the structure.

The system 1100 also includes a metrology processor 1116. In one exemplary embodiment, the processor 1110 can transmit the one or more values of the one or more profile parameters to the metrology processor 1116. The metrology processor 1116 can then adjust one or more process parameters or equipment settings of the first fabrication cluster 1102 based on the one or more values of the one or more profile parameters determined using the optical metrology system 1104. The metrology processor 1116 can also adjust one or more process parameters or equipment settings of the second fabrication cluster 1106 based on the one or more values of the one or more profile parameters determined using the optical metrology system 1104. As noted above, the second fabrication cluster 1106 can process the wafer before or after the first fabrication cluster 1102. In another exemplary embodiment, the processor 1110 is configured to train a machine learning system 1114 using the set of measured diffraction signals as inputs to the machine learning system 1114 and profile parameters as the expected outputs of the machine learning system 1114.

One or more components of the system 1100 can include or implement embodiments of the invention as described herein. In one embodiment the system 1100 includes logic to compute background electric or magnetic fields of an environment of the diffracting structure based on a model of the diffracting structure, compute scattered electric or magnetic fields from the diffracting structure using a scattered field formulation based on the computed background fields, compute spectral information for the model of the diffracting structure based on the computed scattered fields, compare the computed spectral information for the model with measured spectral information for the diffracting structure; and in response to a good model fit, determine a physical characteristic of the diffracting structure based on the model of the diffracting structure. For example, a processor (e.g., the processor 1110) can be configured to evaluate the diffracting structure according to a methods described herein.

Thus, electromagnetic modeling of finite structures and finite illumination for metrology and inspection are described. As explained above, dramatic simulation speedup may be obtained for non-periodic targets on top of or embedded within a substrate having one or more films.

It is to be understood that the above description is intended to be illustrative, and not restrictive. Many other embodiments will be apparent to those of skill in the art upon reading and understanding the above description. Although the present invention has been described with reference to particular embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A computer implemented method of evaluating a diffracting structure, the method comprising:
   providing a scatterometry model of the diffracting structure using an optical metrology system;
   computing, with the optical metrology system, spectral information for the scatterometry model of the diffracting structure, including:
      computing background electric or magnetic fields of an environment of the diffracting structure, computing scattered electric or magnetic fields from the diffracting structure using a scattered field formulation based on the computed background fields, and computing spectral information for the scatterometry model of the diffracting structure based on the computed scattered fields;

measuring spectral information for the diffracting structure using the optical metrology system, including illuminating the diffracting structure with a light source, and measuring spectral information for the diffracting structure with a detector;

comparing the computed spectral information for the scatterometry model with the measured spectral information for the diffracting; and in response to a good model fit based on the comparison between the computed spectral information and the measured spectral information, determining a physical characteristic of the diffracting structure using the scatterometry model of the diffracting structure.

2. The method of claim 1, wherein computing the background electric or magnetic fields of the environment comprises computing electric or magnetic fields for free space.

3. The method of claim 1, wherein computing the background electric or magnetic fields of the environment comprises computing electric or magnetic fields of one or more films disposed under the diffracting structure.

4. The method of claim 1, wherein computing the background and scattered fields comprises computing the background and scattered fields for multiple angles of incidence at once.

5. The method of claim 1, wherein computed incident radiation comprises finite beam illumination or plane-wave incident illumination.

6. The method of claim 1, wherein:
the diffracting structure comprises a periodic region and a non-periodic region;
computing the background fields of the environment comprises computing the background fields of the environment of the diffracting structure in the periodic region using rigorous coupled-wave analysis (RCWA); and
computing the scattered fields comprises computing the scattered fields from the diffracting structure in the non-periodic region using the scattered field formulation based on the computed background fields.

7. The method of claim 6, further comprising determining fields of the periodic and non-periodic regions of the diffracting structure by applying domain decomposition to the fields for the periodic and non-periodic regions.

8. The method of claim 1, wherein computed incident radiation comprises coherent or partially coherent illumination.

9. The method of claim 8, further comprising:
computing speckle fields and line edge roughness for the diffracting structure based on the coherent or partially coherent illumination.

10. The method of claim 1, wherein computing the background electric or magnetic fields at a given point comprises:
decomposing modeled incident illumination into a set of plane waves;
propagating the set of plane waves from a predetermined initial point to the given point; and
summing the propagated set of plane waves at the given point.

11. The method of claim 10, wherein decomposing the modeled incident illumination into the set of plane waves comprises a discrete decomposition.

12. The method of claim 10, wherein decomposing the modeled incident illumination into the set of plane waves comprises a continuous decomposition.

13. The method of claim 1, wherein providing the scatterometry model of the diffracting structure comprises discretizing the diffracting structure into a mesh.

14. The method of claim 13, wherein discretizing the diffracting structure into the mesh comprises refining the mesh in an area with a defect.

15. The method of claim 13, wherein subsequent model iterations comprise scaling the mesh.

16. A non-transitory machine-readable storage medium having instructions stored thereon which cause a computer to perform a method of evaluating a diffracting structure, the method comprising:
providing a scatterometry model for the diffracting structure using an optical metrology system;
computing, with the optical metrology system, spectral information for the scatterometry model of the diffracting structure, including:
computing background electric or magnetic fields of an environment of the diffracting structure,
computing scattered electric or magnetic fields from the diffracting structure using a scattered field formulation based on the computed background fields, and
computing spectral information for the scatterometry model of the diffracting structure based on the computed scattered fields;
measuring spectral information for the diffracting structure using the optical metrology system, including illuminating the diffracting structure with a light source, and measuring spectral information for the diffracting structure with a detector;
comparing the computed spectral information for the scatterometry model with the measured spectral information for the diffracting structure; and
in response to a good model fit based on the comparison between the computed spectral information and the measured spectral information, determining a physical characteristic of the diffracting structure using the scatterometry model of the diffracting structure.

17. The non-transitory machine-readable storage medium of claim 16, wherein computing the background electric or magnetic fields of the environment comprises computing electric or magnetic fields for free space.

18. The non-transitory machine-readable storage medium of claim 16, wherein computing the background electric or magnetic fields of the environment comprises computing electric or magnetic fields of one or more films disposed under the diffracting structure.

19. The non-transitory machine-readable storage medium of claim 16, wherein computing the background electric or magnetic fields at a given point comprises:
decomposing modeled incident illumination into a set of plane waves;
propagating the set of plane waves from a predetermined initial point to the given point; and
summing the propagated set of plane waves at the given point.

20. An optical measurement system comprising:
a light source to illuminate a diffracting structure;
a detector to measure spectral information for the diffracting structure;

first logic to receive the measured spectral information for the diffracting structure; and second logic to:

provide a scatterometry model of the diffracting structure;

compute spectral information for the scatterometry model, including computing background electric or magnetic fields of an environment of the diffracting structure based on a model of the diffracting structure, computing scattered electric or magnetic fields from the diffracting structure using a scattered field formulation based on the computed background fields, and computing spectral information for the scatterometry model of the diffracting structure based on the computed scattered fields;

compare the computed spectral information for the scatterometry model with the measured spectral information for the diffracting structure; and in response to a good model fit based on the comparison between the computed spectral information and the measured spectral information, determine a physical characteristic of the diffracting structure using the scatterometry model of the diffracting structure.

21. The optical measurement system of claim 20, wherein the second logic is to compute the background electric or magnetic fields of the environment by computing electric or magnetic fields for free space.

22. The optical measurement system of claim 20, wherein the second logic is to compute the background electric or magnetic fields of the environment by computing electric or magnetic fields of one or more films disposed under the diffracting structure.

23. The optical measurement system of claim 20, wherein the second logic is to compute the background electric or magnetic fields at a given point by:

decomposing modeled incident illumination into a set of plane waves;

propagating the set of plane waves from a predetermined initial point to the given point; and summing the propagated set of plane waves at the given point.

* * * * *